(12) United States Patent
Baratella et al.

(10) Patent No.: US 10,221,132 B2
(45) Date of Patent: Mar. 5, 2019

(54) PROCESS FOR THE PREPARATION OF A SULFUR-AMINE

(71) Applicant: Chemelectiva Srl, Novara (IT)

(72) Inventors: Marco Baratella, Novara (IT); Mauro Gaboardi, Novara (IT); Graziano Castaldi, Novara (IT); Erminio Oldani, Novara (IT)

(73) Assignee: CHEMELECTIVA SRL, Norvara (NO) (IT)

( * ) Notice: Subject to any disclaimer, the term of this patent is extended or adjusted under 35 U.S.C. 154(b) by 0 days.

(21) Appl. No.: 15/789,023

(22) Filed: Oct. 20, 2017

(65) Prior Publication Data

US 2018/0111897 A1    Apr. 26, 2018

(30) Foreign Application Priority Data

Oct. 24, 2016    (IT) .................. 102016000106709

(51) Int. Cl.
| | | |
|---|---|---|
| C07C 319/06 | (2006.01) | |
| C07C 327/30 | (2006.01) | |
| C07C 303/28 | (2006.01) | |
| C07C 227/02 | (2006.01) | |
| C07C 269/04 | (2006.01) | |
| C07C 319/02 | (2006.01) | |

(52) U.S. Cl.
CPC .......... *C07C 319/06* (2013.01); *C07C 227/02* (2013.01); *C07C 269/04* (2013.01); *C07C 303/28* (2013.01); *C07C 319/02* (2013.01); *C07C 327/30* (2013.01)

(58) Field of Classification Search
None
See application file for complete search history.

(56) References Cited

FOREIGN PATENT DOCUMENTS

| EP | 0044203 A1 | 1/1982 |
|---|---|---|
| EP | 0054409 A1 | 6/1982 |
| JP | 05255238 | * 10/1993 |

OTHER PUBLICATIONS

English Machine Translation of JP 05255238, Kuwazuka et al., 1993 (Year: 1993).*
Vedejs et al., "Synthesis of azocine derivatives from thio aldehyde Diels-Alder adducts", The Journal of Organic Chemistry, 1988, vol. 53, No. 10, pp. 2226-2232.
Brower et al., "Synthesis and evaluation of chloromethyl sulfoxides as a new class of selective irreversible cysteine protease inhibitors", Bioorganic & Medicinal Chemistry, 2007, vol. 15, No. 22, pp. 6985-6993.
Italian Search Report and Written Opinion for Corresponding Italian Application No. IT 201600106709 (8 Pages) (dated Jul. 4, 2017).

* cited by examiner

*Primary Examiner* — Sudhakar Katakam
*Assistant Examiner* — Jennifer C Sawyer
(74) *Attorney, Agent, or Firm* — Lucas & Mercanti, LLP

(57) ABSTRACT

The present invention relates to a process for the synthesis of cysteamine or a salt thereof.

20 Claims, No Drawings

PROCESS FOR THE PREPARATION OF A SULFUR-AMINE

CROSS-REFERENCE TO RELATED APPLICATIONS

This application claims the benefit of Italian Patent Application No. 102016000106709 filed Oct. 24, 2016, the contents of which are incorporated herein by reference.

FIELD OF THE INVENTION

The present invention relates to a process for the synthesis of a cysteamine salt, in particular cysteamine bitartrate, a drug mainly used for the treatment of nephropathic cystinosis.

BACKGROUND OF THE INVENTION

Cystinosis belongs to the group of diseases known as inborn errors of metabolism. Said disease affects the metabolism of cystine and develops in particular when the transport system of cystine outside lysosomes does not act properly, leading to cystine accumulation inside the cells of the organism. This causes a malfunction of the majority of the organs. The first organs to be affected are kidneys and eyes, subsequently also thyroid, liver, muscles, pancreas and central nervous system are involved.

Three clinical forms of cystinosis have been classified: infantile or nephropathic, tardive and benign.

The infantile or nephropathic cystinosis is the most frequent (about 95% of cases) and severe form of cystinosis. The symptoms appear between the sixth and the eighteenth month of life, the first to become apparent are anorexia, vomiting, excessive thirst and urination, growth difficulty, rickets and episodes of dehydration. These symptoms are caused by a disorder called renal tubulopathy or Fanconi's syndrome that is a failure of renal tubules in the absorption of nutrients and minerals, thereby being dispersed in urine. Corneal deposits of cystine produce crystals which cause photophobia and lacrimation. Without a specific treatment, children with cystinosis develop an end-stage kidney failure that is the loss of renal function from six to twelve years of age.

The administration of cysteamine bitartrate represents the unique specific treatment which allows to control cystinosis primary lesion, which is the accumulation of cystine into lysosomes, delaying or even preventing renal failure. The more early the treatment is started, the more effective it will be, possibly before the age of two, when the renal function is still intact or little affected.

Cysteamine bitartrate is a compound of formula (I)

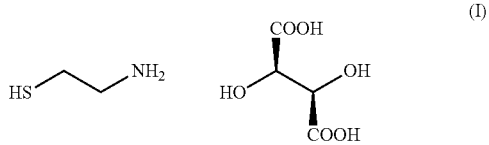

(I)

marketed as Cystagon®.

There are several processes known in the art for the synthesis of cysteamine. For example, EP 0 044 203 discloses a process for the synthesis of a cysteamine salt according to Scheme 1 below Scheme 1

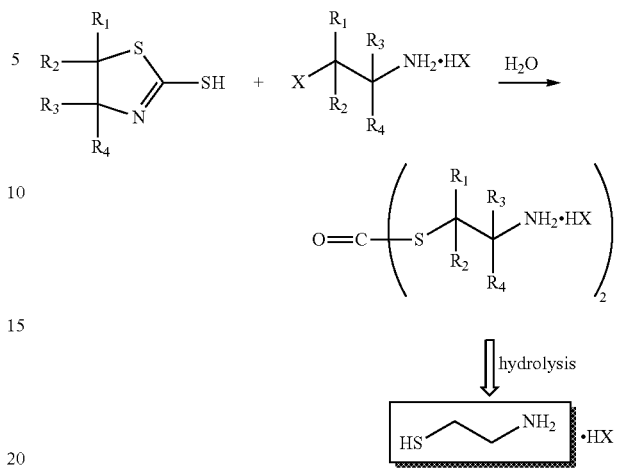

where $R_1$, $R_2$, $R_3$ and $R_4$ can be the same or different and each represents a hydrogen atom, a lower alkyl group, also hydroxyl substituted, or a phenyl group, and X represents a halogen atom.

EP 0 054 409, instead, discloses the process for the synthesis of cysteamine reported in the following Scheme 2

Scheme 2

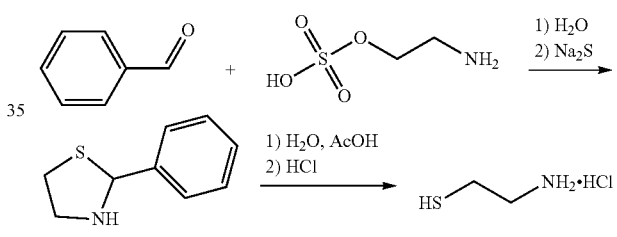

Furthermore, Italian patent IT 1 117 224 discloses a process for the synthesis of cysteamine hereinafter reported in Scheme 3

Scheme 3

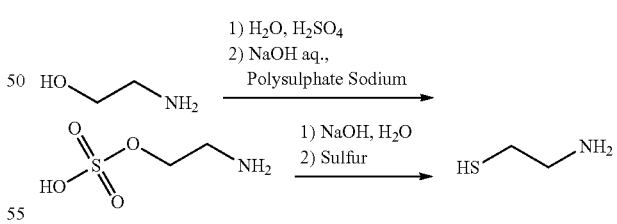

The processes for the synthesis of cysteamine or salts thereof above disclosed show some significant drawbacks among which the complexity of the starting compounds used and the difficulty in procuring them commercially. Moreover, in said processes some harmful and dangerous reagents for man and environment are employed, which prevent them to be used on industrial scale.

The purpose of the present invention is to provide a process for the synthesis of cysteamine or a salt thereof which overcomes the drawbacks and disadvantages of those known in the art.

It was surprisingly found a process which overcomes the problems of those known in the art. Said process in fact has simple synthetical steps, with high selective reactions, and moreover imply the use of simple and easily available starting compounds allowing to obtain cysteamine or a salt thereof, in particular cysteamine bitartrate, with high yield and purity. Therefore, said novel process is particularly suitable for the application on industrial scale.

OBJECT AND SUMMARY OF THE INVENTION

Therefore, an object of the present invention is a process for the synthesis of cysteamine or a salt thereof comprising:
a) the protection reaction of the amine group in the compound of formula (V)

to obtain the compound of formula (IV)

b) the tosylation reaction of the hydroxyl group in the compound of formula (IV) to obtain the compound of formula (III)

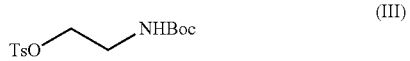 [SMILES: Cc1ccc(S(=O)(=O)OCCNC(=O)OC(C)(C)C)cc1]

c) the nucleophilic substitution reaction in the compound of (III), to obtain the compound of formula (II)

d) the hydrolysis reaction of the compound of formula (II) to obtain cysteamine or a salt thereof.

DETAILED DESCRIPTION OF THE INVENTION

According to the present invention, a salt of cysteamine is a pharmaceutical acceptable salt thereof, typically selected from the group consisting of hydrochloride, hydrobromide, tartrate, bitartrate, fumarate, and succinate. Preferably, a salt of cysteamine according to the present invention is the hydrochloride salt or the bitartrate salt.

In step a) of the process object of the present invention, the protection reaction is carried out in the presence of di-tert-butyl dicarbonate ((Boc)$_2$O) and in the presence of an apolar solvent selected from the group consisting of toluene, tetrahydrofuran, dichloromethane, ethyl acetate, preferably toluene.

In step b) of the process object of the present invention, the tosylation reaction is carried out with p-toluenesulphonyl chloride, in the presence of a base and of an apolar solvent.

The base used in step b) can be an organic base typically selected from the group consisting of triethylamine, tributylamine, diisopropylamine, pyridine, or an inorganic base, for example, potassium carbonate, sodium carbonate, sodium bicarbonate. According to a preferred embodiment of the present invention, the base used in step b) is an organic base and, in particular, is triethylamine.

The apolar solvent used in step b) is selected from the group consisting of toluene, tetrahydrofuran, dichloromethane, ethyl acetate and it is preferably toluene.

In step c) of the process object of the present invention, the nucleophilic substitution reaction is typically carried out with thioacetic acid, potassium thioacetate or sodium thioacetate, preferably with potassium thioacetate in the presence of a base and of a polar solvent.

The base used in step c) is selected from the group consisting of potassium carbonate, sodium carbonate, sodium bicarbonate and preferably is potassium carbonate.

The polar solvent used in step c) is selected from the group consisting of dimethyl sulfoxide, dimethylformamide, dimethylacetamide, acetonitrile and preferably is dimethyl sulfoxide.

In step d) of the process object of the present invention, the hydrolysis reaction is carried out in the presence of an acid in a polar protic solvent.

The acid used in step d) is typically selected from the group consisting of hydrochloric acid, hydrobromic acid, trifluoroacetic acid or mixtures thereof and it is preferably hydrochloric acid.

The polar protic solvent used in step d) is selected from the group consisting of water, methanol, ethanol, isopropanol, n-butanol, t-butanol and it is preferably n-butanol.

Cysteamine obtained according to step d) is typically cysteamine in salt form. Preferably, cysteamine obtained according to step d) is cysteamine hydrochloride. According to a particularly preferred embodiment of the invention, the cysteamine salt obtained according to step d) can be converted into another cysteamine salt. More preferably, cysteamine hydrochloride obtained according to step d) is converted into cysteamine bitartrate.

The conversion of a cysteamine salt obtained according to step d) into another cysteamine salt can be carried out according to methods known in the art.

In particular, the conversion of cysteamine hydrochloride into cysteamine bitartrate is carried out in the presence of a base and tartaric acid, in the presence of alcohols, mixtures thereof, or in the presence of a mixture of water and alcohols.

The base used in said conversion process is typically selected from the group consisting of triethylamine, tributylamine, and preferably is tributylamine.

Alcohols used in the conversion reaction are selected from the group consisting of methanol, ethanol, isopropanol, or mixture thereof.

Preferably a mixture of isopropanol and methanol is used.

Although the invention has been described in its characterising aspects, changes and equivalents evident to the skilled in the art are encompassed by the present invention.

The present invention will be now illustrated by means of some examples, which are not intended to limit the scope of the invention. All the terms used in the present application, unless otherwise provided, are to be understood in their common meaning as known in the art. Other specific definitions for some terms, as used in the present application, are pointed out below and are to be applied constantly for all the description and the claims, unless a different definition explicitly provides a broader definition.

EXAMPLES

Example 1: Synthesis of (tert-butoxycarbonyl) ethanolamine of Formula (IV)

In a reaction flask, ethanolamine (50.00 g, 0.82 mol) and toluene (250.00 ml) were loaded, the temperature was cooled to about 10° C. and a solution of di-tert-butyl dicarbonate (176.66 g, 0.82 mol) in toluene (250 ml) was added. The temperature was raised to about 25° C. and the reaction mixture was maintained under these conditions for about five hours. Once the reaction is finished, water (250.00 ml) was added and the organic phase was washed with water (3×250.00 ml). The collected organic phases were concentrated till residue through vacuum distillation to give 121.40 g of (tert-butoxycarbonyl) ethanolamine.

$^1$H-NMR (CDCl$_3$, 300 MHz): δ 3.62 (t, 2H), 3.21 (t, 2H), 1.40 (s, 9H).

Example 2: Synthesis of 2-[(tert-butoxycarbonyl)amino]ethyl 4-methylbenzenesulfonate of formula (III)

In a reaction flask, (tert-butoxycarbonyl)-ethanolamine (121.40 g, 0.75 mol), toluene (600.00 ml), triethylamine (124.46 g, 1.23 mol) were loaded, and the temperature was raised to about 40° C. A solution of p-toluenesulphonyl chloride (214.48 g, 1.12 mol) in toluene (600.00 ml) was added and the reaction mixture was maintained under these conditions for about six hours. Once the reaction is finished, the temperature was cooled to about 20° C., water (200.00 ml) was added and the organic phase was washed with water (1×200.00 ml), with an aqueous solution of 2N hydrochloric acid (1×240.00 ml) and with water again (2×200.00 ml), the collected organic phases were concentrated till residue through vacuum distillation to give 287.00 g of 2-[(tert-butoxycarbonyl)amino]ethyl 4-methylbenzensulphonate.

$^1$H-NMR (CDCl$_3$, 300 MHz): δ 7.77 (d, 2H), 7.31 (d, 2H), 4.04 (t, 2H), 3.35 (t, 2H), 2.42 (s, 3H), 1.41 (s, 9H).

Example 3: Synthesis of S-2-(tert-butoxycarbonylamino)ethyl-ethantionate of formula (II)

In a reaction flask, 2-[(tert-butoxycarbonyl)amino]ethyl 4-methylbenzensulphonate (18.00 g, 0.057 mol), dimethyl sulfoxide (95.00 ml) were loaded, the temperature was cooled to about 15° C., potassium carbonate (12.60 g, 0.091 mol) was added, potassium thioacetate (8.46 g, 0.074 mol) and the reaction mixture was maintained under these conditions for about two hours. Once the reaction is finished, a mixture of water and ice (114 g) was added at the temperature of about 10° C. and the aqueous phase was extracted with toluene (2×72 ml). The organic phase was washed with water (4×36 ml) and the collected organic phase were concentrated till residue through vacuum distillation to give 12 g di S-2-(tert-butoxycarbonyl amino)ethyl-ethantionate.

$^1$H-NMR (CDCl$_3$, 300 MHz): δ 3.25 (t, 2H), 2.97 (t, 2H), 2.31 (s, 3H), 1.43 (s, 9H).

Example 4: Synthesis of Cysteamine Hydrochloride

In a reaction flask, S-2-(tert-butoxycarbonyl amino)ethyl-ethantionate (45.5 g, 0.17 mol), n-butanol (315.00 ml) and an aqueous solution of 37% hydrochloric acid (34.29 g, 0.35 mol) were loaded, the temperature was raised to 75° C. and the reaction mixture was maintained under these conditions for about six hours. Once the reaction is finished, the solvent and the residual water are removed through vacuum distillation, the temperature was cooled to 10° C. and n-butanol was added (40.00 ml); the resulting solid was filtered, washed with n-butanol (2×10.00 ml) and dried in oven under vacuum at about 40° C. to give 17.80 g of cysteamine hydrochloride.

$^1$H-NMR (D$_2$O, 300 MHz): δ 3.18 (t, 2H), 2.83 (t, 2H).

Example 5. Synthesis of Cysteamine Bitartrate

In a reaction flask, Cysteamine hydrochloride (75.00 g, 0.66 mol), isopropanol (750.00 ml), methanol (750.00 ml), tributylamine (127.89 g, 0.69 mol), and tartaric acid (103.52 g, 0.69 mol) were loaded, the temperature was raised to about 70° C. and the reaction mixture was maintained under these conditions for about thirty minutes. Once the reaction is finished, the temperature was cooled to about 25° C., the resulting solid was filtered, washed with a solution of methanol and isopropanol 1:1 (2×200.00 ml) and dried in oven under vacuum at 40° C. to give 111.00 g of Cysteamine bitartrate.

$^1$H-NMR (D$_2$O, 300 MHz): δ 4.53 (s, 2H), 3.19 (t, 2H), 2.82 (t, 2H).

The invention claimed is:
1. A process for the synthesis of cysteamine or a salt thereof comprising:
 a) the protection reaction of the amine group in the compound of formula (V)

to obtain the compound of formula (IV)

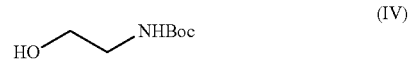

b) the tosylation reaction of the hydroxyl group in the compound of formula (IV) to obtain the compound of formula (III)

c) the nucleophilic substitution reaction in the compound of formula (III), to obtain the compound of formula (II)

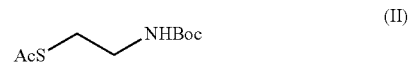

d) the hydrolysis reaction of the compound of formula (II) to give cysteamine or a salt thereof.
2. A process according to claim 1 wherein the cysteamine salt is a pharmaceutically acceptable salt thereof selected from the group consisting of hydrochloride, hydrobromide, tartrate, bitartrate, fumarate, and succinate salt.
3. A process according to claim 2 wherein the cysteamine salt is hydrochloride or bitartrate salt.

4. A process according to claim 1 wherein in step a) the protection reaction is carried out in the presence of di-tert-butyl dicarbonate ((Boc)$_2$O) and in the presence of an apolar solvent selected from the group consisting of toluene, tetrahydrofuran, dichloromethane, and ethyl acetate.

5. A process according to claim 4 wherein the apolar solvent is toluene.

6. A process according to claim 1 wherein in step b) the tosylation reaction is carried out with p-toluenesulfonyl chloride, in the presence of a base and of an apolar solvent.

7. A process according to claim 6 wherein the base is an organic base selected from the group consisting of triethylamine, tributylamine, diisopropylamine, pyridine, or an inorganic base selected from the group consisting of potassium carbonate, sodium carbonate, and sodium bicarbonate.

8. A process according to claim 6 wherein the apolar solvent is selected from the group consisting of toluene, tetrahydrofuran, dichloromethane, and ethyl acetate.

9. A process according to claim 7 wherein the base is triethylamine and the apolar solvent is toluene.

10. A process according to claim 1 wherein the nucleophilic substitution reaction at step c) is carried out with thioacetic acid, potassium thioacetate or sodium thioacetate, in the presence of a base and of a polar solvent.

11. A process according to claim 10 wherein the base is selected from the group consisting of potassium carbonate, sodium carbonate and sodium bicarbonate.

12. A process according to claim 10 wherein the polar solvent is selected from the group consisting of dimethyl sulfoxide, dimethylformamide, dimethylacetamide and acetonitrile.

13. A process according to claim 1 wherein in step d) the hydrolysis reaction is carried out in the presence of an acid in a polar protic solvent.

14. A process according to claim 13 wherein the acid is selected from the group consisting of hydrochloric acid, hydrobromic acid, trifluoroacetic acid and mixtures thereof.

15. A process according to claim 13 wherein the polar protic solvent is selected from the group consisting of water, methanol, ethanol, isopropanol, n-butanol, and t-butanol.

16. A process according to claim 14 wherein the acid is hydrochloric acid and the polar protic solvent is n-butanol.

17. A process according to claim 1 wherein the cysteamine salt obtained according to step d) is converted into another cysteamine salt.

18. A process according to claim 17 wherein cysteamine hydrochloride is converted into cysteamine bitartrate.

19. A process according to claim 18 wherein the conversion of cysteamine hydrochloride into cysteamine bitartrate is carried out in the presence of a base and tartaric acid, in the presence of alcohols or alcohol mixtures, or in the presence of a mixture of water and alcohols.

20. A process according to claim 19 wherein the conversion of cysteamine hydrochloride into cysteamine bitartrate is carried out in the presence of a mixture of isopropanol and methanol.

* * * * *